(12) United States Patent
Lahaut

(10) Patent No.: US 7,073,372 B2
(45) Date of Patent: Jul. 11, 2006

(54) ONLINE ROTATING VISCOMETER AND ASSOCIATED MEASUREMENT METHODS

(75) Inventor: Hugues Lahaut, Ixelles (BE)

(73) Assignee: MLD Research, Bruxelles (BE)

( * ) Notice: Subject to any disclaimer, the term of this patent is extended or adjusted under 35 U.S.C. 154(b) by 104 days.

(21) Appl. No.: 10/478,029

(22) PCT Filed: May 17, 2002

(86) PCT No.: PCT/BE02/00081

§ 371 (c)(1),
(2), (4) Date: Apr. 15, 2004

(87) PCT Pub. No.: WO02/095366

PCT Pub. Date: Nov. 28, 2002

(65) Prior Publication Data

US 2004/0177679 A1    Sep. 16, 2004

(30) Foreign Application Priority Data

May 18, 2001    (EP) .................................. 01870106

(51) Int. Cl.
*G01N 11/14* (2006.01)

(52) U.S. Cl. ...................................................... 73/54.28
(58) Field of Classification Search ............... 73/54.28, 73/54.35
See application file for complete search history.

(56) References Cited

U.S. PATENT DOCUMENTS

| | | | | |
|---|---|---|---|---|
| 3,435,666 A | * | 4/1969 | Fann .......................... | 73/54.39 |
| 4,557,142 A | * | 12/1985 | Hensley et al. .......... | 73/152.19 |
| 4,648,263 A | * | 3/1987 | Deysarkar et al. ......... | 73/54.35 |
| 4,823,594 A | * | 4/1989 | Gray .......................... | 73/54.01 |
| 5,365,777 A | * | 11/1994 | Layton ....................... | 73/54.28 |
| 5,481,903 A | * | 1/1996 | King et al. ................. | 73/54.28 |
| 5,513,517 A | * | 5/1996 | Van Meter et al. ........ | 73/54.28 |
| 5,535,619 A | * | 7/1996 | Brookfield ................. | 73/54.33 |
| 5,540,088 A | * | 7/1996 | Hall ............................ | 73/54.43 |
| 5,684,247 A | | 11/1997 | Preikschat ................. | 73/54.32 |
| 5,874,665 A | * | 2/1999 | Larsson ..................... | 73/54.28 |

* cited by examiner

*Primary Examiner*—Hezron Williams
*Assistant Examiner*—John Fitzgerald
(74) *Attorney, Agent, or Firm*—Olson & Hierl, Ltd.

(57) ABSTRACT

Rotating type viscosimeter having a motor (2) for driving a rotating assembly (3) extending through an aperture (4) into a liquid to be tested (1) and measuring the shear forces imparted by said liquid (1) to the rotating assembly (3). In order to prevent said liquid (1) from leaking through the aperture (4) due to a liquid pressure (p1) at the level of the aperture (4), the viscosimeter comprises means for creating a counter-pressure (p2) at the level of a gap between the rotating assembly (3) and the aperture (4). Thanks to this counter-pressure (p2), no solid sealing means are required, thereby improving the durability and the robustness of the viscosimeter, as well as simplifying it by eliminating countermeasures otherwise needed for taking into account parasitic friction forces exerted on the rotating assembly (3) due to such solid sealing means.

20 Claims, 7 Drawing Sheets

ONLINE ROTATING VISCOMETER AND ASSOCIATED MEASUREMENT METHODS

FIELD OF THE INVENTION

The invention relates to a viscosimeter comprising a motor for driving an assembly in a rotary movement, said assembly extending at least partially into a liquid to be tested through an aperture of a partition for separating the liquid from the motor.

DESCRIPTION OF PRIOR ART

Such viscosimeters are known from prior art and are often referred to as rotating viscosimeters because they either measure the shear forces imparted by the liquid on a part of the rotating assembly in contact with the liquid, usually a form of impeller, or on a further part in reaction to this rotation, said shear forces reflecting the viscosity of the liquid.

In case the liquid to be tested is contained in a container and the liquid level is able to come above the level of the aperture or in case said liquid flows through a pipeline, such known rotating viscosimeters often comprise gaskets for preventing the liquid from escaping through the aperture. Gaskets are well known for being an important source of trouble, particularly when they are in contact with assemblies having a relative movement with them and/or when the liquid has strong abrasive properties. Moreover, the frictional forces between such gaskets and the rotating assembly negatively influences the accuracy of the viscosity measurement by introducing a parasitic torque which varies a.o. with operating conditions and time.

Means for eliminating this parasitic torque have been disclosed, for example, by Brookfield, an American company. Brookfield uses two concentric shafts, an outer drive shaft and an inner sensor shaft. The drive shaft provides the main rotational driving force to the impeller and shields the inner sensor shaft from the frictional forces between the drive shaft and an outer gasket material.

Another example of such known viscosimeters is described in patent number U.S. Pat. No. 5,684,247. This exemplary viscosimeter comprises three concentric shafts, and two gaskets, thereby making the system even more complicated.

Though such known viscosimeters work well in many circumstances, they are of a complicated construction and they may not deliver the durability and robustness required for industrial applications.

SUMMARY OF THE INVENTION

It is an object of the invention to provide a viscosimeter with a simplified construction, with a higher durability and with a better robustness with regard to corrosion and/or abrasion form the liquid to be tested.

To this end, the viscosimeter according to the invention is characterized in that it comprises means for creating a counter-pressure at a motor side of the partition for preventing the liquid from escaping through the aperture, the level of the liquid being—in operation—above the level of the aperture.

When the liquid to be tested is in a container and the level of the liquid comes above the level of the aperture through which the rotating assembly extends, said liquid exerts a pressure at the level of the aperture at a liquid side of the partition, which would naturally cause the liquid to leak through the aperture. By creating a counter-pressure at the motor side of the partition, the liquid pressure is counterbalanced, thereby stopping any leakage of the liquid. A gasket or any other form of solid seal surrounding the rotating assembly becomes thus superfluous.

The absence of a gasket greatly improves the durability and the robustness of the viscosimeter. In the absence of a gasket, the aforementioned problem of parasitic torque is also eliminated. The rotating assembly can therefore be simplified. A simple single shaft may, for example, be used for transmitting the rotary movement from the motor to the impeller.

When the liquid to be tested is transported in a pipeline, similar problems occur for measuring the viscosity of the liquid directly in the pipeline. The viscosimeter according to the invention solves these problems in a similar way, i.e. by applying a counter-pressure at the motor side for counterbalancing the liquid pressure at the level of an aperture created in the pipeline for passing through the rotating assembly.

In many cases, the pressure exerted by the liquid at the level of the aperture is variable. This is for example the case when a tank is filled up with the liquid to be tested and conversely when the tank is emptied. Therefore, in preferred embodiments, the means for creating the counter-pressure comprises means for regulating said counter-pressure.

SHORT DESCRIPTION OF THE DRAWINGS

Figure 6A:
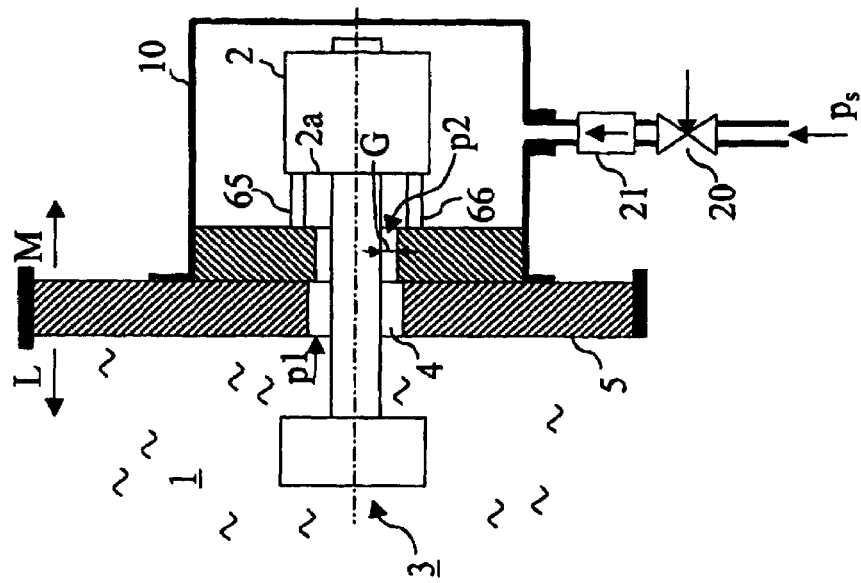
Figure 6B:
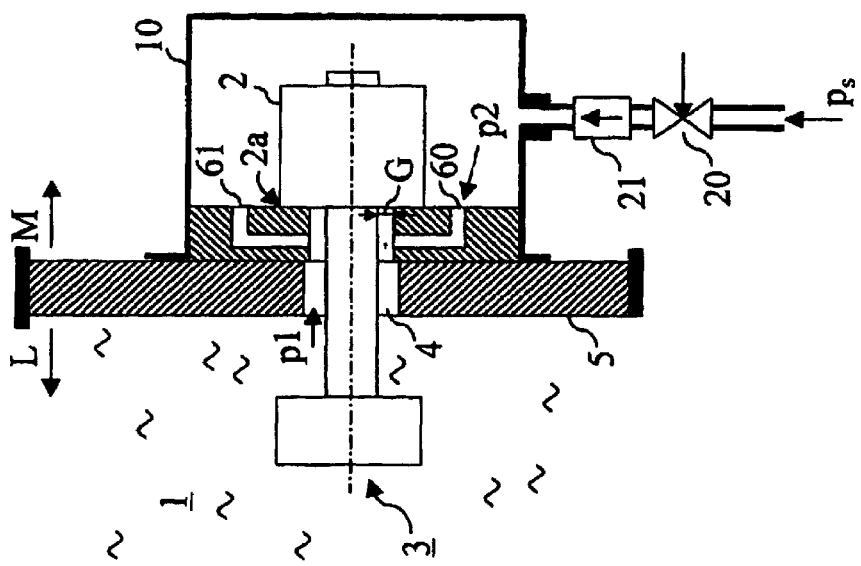
Figure 7:
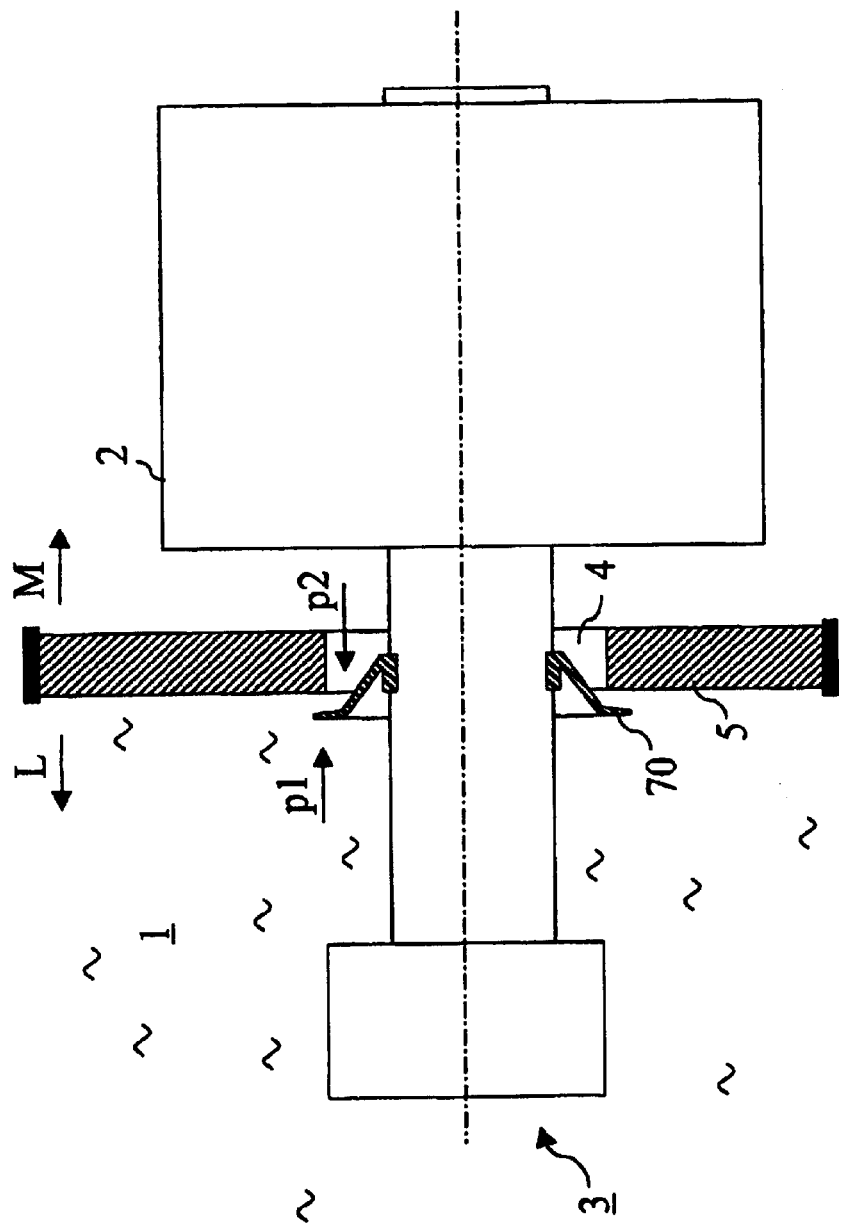

FIG. 6*a* and 6*b* show two exemplary arrangements of the motor with regard to the partition in an embodiment according to the invention, and FIG. 7 shows an embodiment of a viscosimeter according to the invention with a safety membrane.

The figures are not drawn to scale. Generally, identical components are denoted by the same reference numerals in the figures.

DETAILED DESCRIPTION OF PREFERRED EMBODIMENTS

Figure 1:
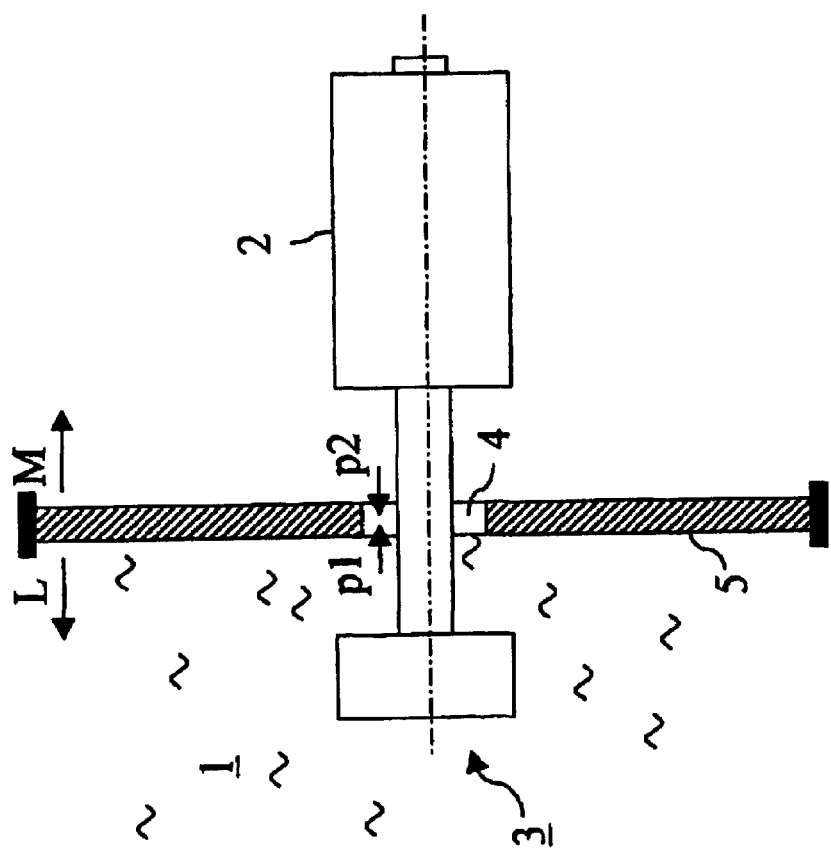
FIG. 1 shows a rotating type viscosimeter according to an embodiment of present invention.

FIG. 1 shows schematically a rotating viscosimeter according to the invention and set up for the measurement of the viscosity of a liquid to be tested (1). The viscosimeter comprises a motor (2) for driving a rotating assembly (3) extending into the liquid to be tested (1) through an aperture (4) of a partition (5) separating the liquid to be tested (1) from the motor (2).

The partition (5) defines thus a separation between a liquid side (L) and a motor side (M), the motor side (M) being the side where one wants to prevent the liquid to be tested (1) to penetrate. At the level of the aperture (4), the liquid to be tested (1) exerts a pressure (p1) on the liquid side (L) which would naturally cause the liquid to be tested (1) to leak through the aperture (4) if there were no means for preventing such leakage. A viscosimeter according to the invention comprises means for creating a counter-pressure (p2) at the motor side (M) and at the level of the aperture (4), such that p2>p1, thereby preventing the liquid to be tested (1) from leaking through the aperture (4). In order not to influence the measurement, the power for creating said counter-pressure (p2) does preferably not originate from the motor (2), but rather from an independent power source. As long as said counter-pressure (p2) is present, which is the case during normal operation of the viscosimeter, there is no contact between the rotating assembly (3) and the partition (5) or any other part attached to the partition (5), neither directly nor indirectly such as via a solid sealing material like a gasket for example. In normal operation, the rotating assembly (3) thus rotates freely into the liquid to be tested (1) without friction forces due to solid sealing means.

Figure 2:
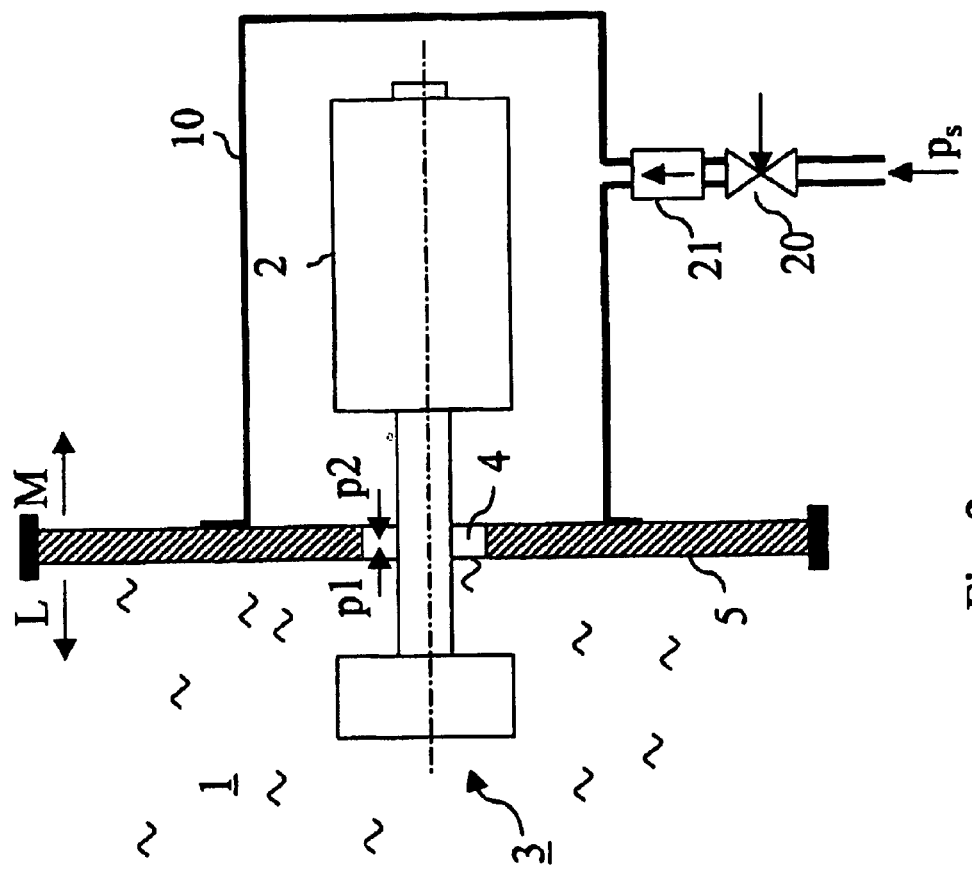
FIG. 2 shows a viscosimeter according to a preferred embodiment of present invention.

An exemplary way for creating such counter-pressure is illustrated on FIG. 2. Here, the viscosimeter comprises a motor housing (10) which encloses the motor (2) hermetically with regard to the partition (5), except for the aperture (4). The motor housing (10) is pressurised by feeding it with compressed air at a supply pressure (ps), such that $ps^3$ p2. A pressure valve (20) can be used for setting the desired counter-pressure (p2). A check-valve (21) may also be used for preventing back-pressure from the motor housing (10) to the compressed air supply system. Such check-valve (21) also serves for maintaining the counter-pressure (p2) in the motor housing (10) in case the supply of compressed air would fail.

Venting of the motor housing (10) usually occurs through the aperture (4), though an additional safety valve can be installed on the motor housing (10).

Figure 3:
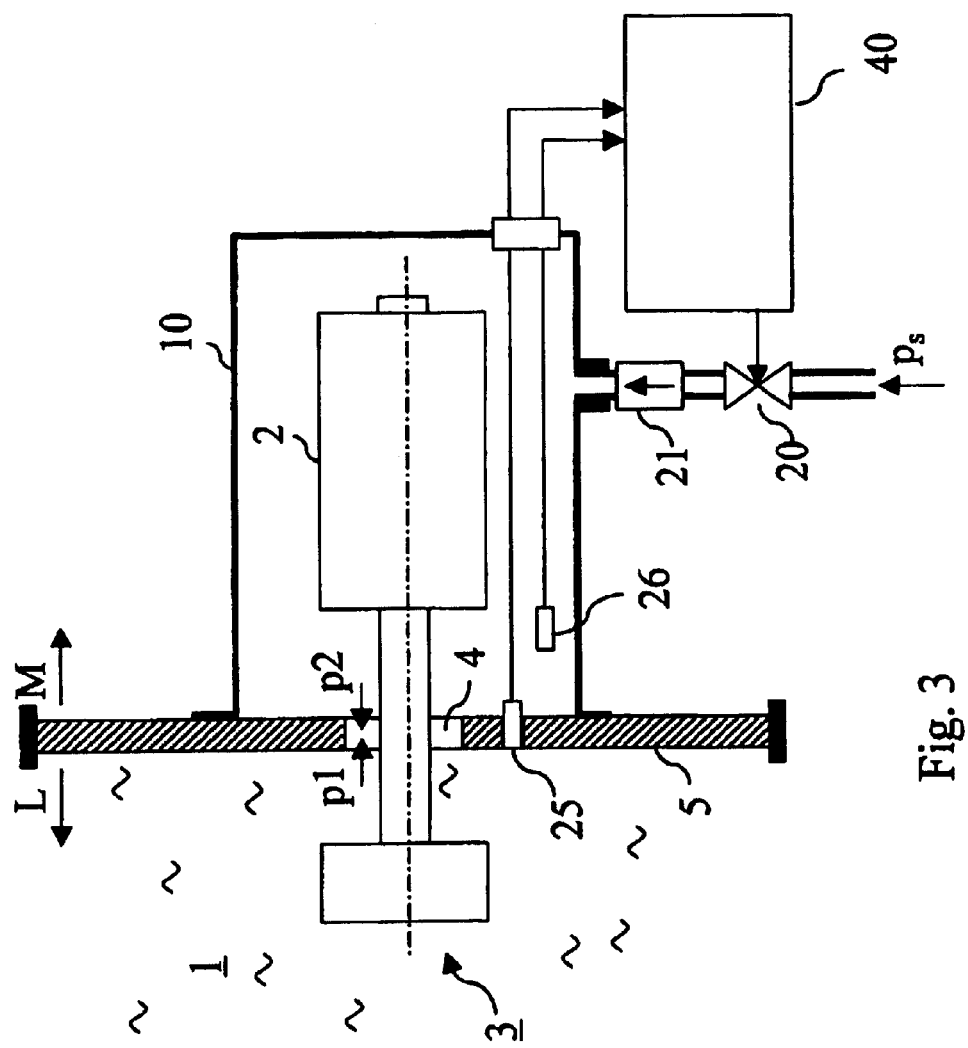
FIG. 3 shows a viscosimeter according to a most preferred embodiment of present invention.

As with most control systems, a closed loop regulation may be required in order to improve the accuracy of the control and/or to improve it's response time. Therefore, in a preferred embodiment, the viscosimeter according to the invention comprises means for regulating the counter-pressure (p2), as illustrated on FIG. 3. Said means for regulating the counter-pressure comprise:

- a liquid pressure sensor (25) for measuring the pressure (p1) exerted by the liquid to be tested (1) on the liquid side (L) at the level of the aperture (4),
- an air pressure sensor (26) for measuring the counter-pressure (p2) at the motor (2) side (M) at the level of the aperture (4),
- means (40) for comparing p1 and p2, and for actuating the pressure valve (20) depending on the results of the comparison and in order to achieve the desired counter-pressure (p2).

Figure 4:
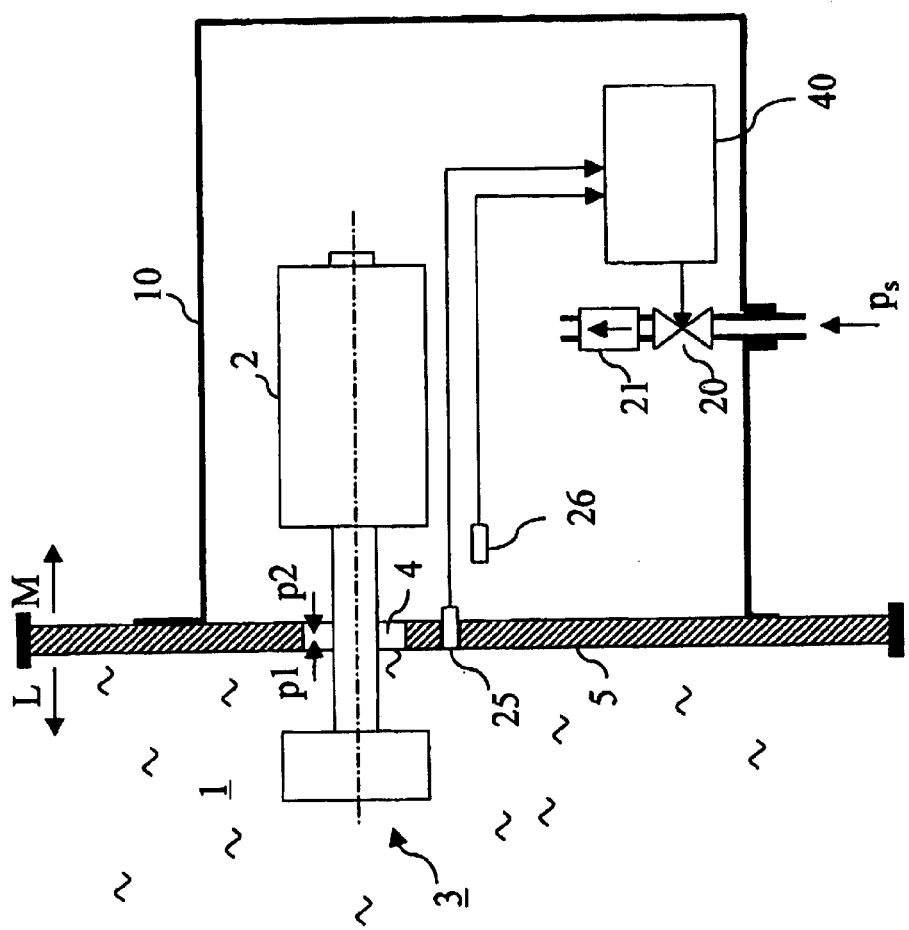
FIG. 4 shows another way of arranging certain components of the viscosimeter of FIG. 3.

There are various ways for arranging those means for regulating the counter-pressure. To take advantage of the pressurisation, it may for example be advantageous to arrange said means as well as the pressure valve (20) and the check-valve (21) into the motor housing (10), as illustrated on FIG. 4.

Figure 5:
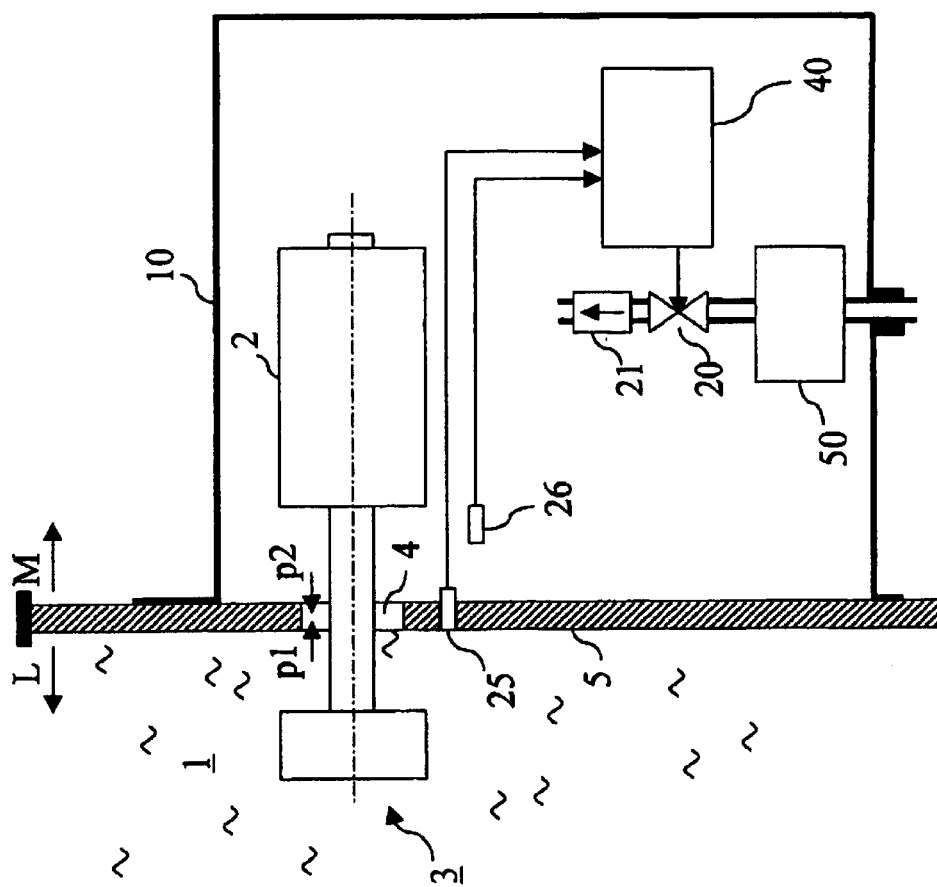
FIG. 5 shows an example of integration of pressure generation means into the motor housing of a viscosimeter according to the invention.

For the same reasons, and/or for further reasons, such as for reasons of integration, it may be advantageous to further arrange means for generating compressed air (50) into the motor housing (10), as illustrated on FIG. 5.

There are also various ways for arranging the motor (2) with regard to the partition (5). In one embodiment, the motor (2) is so arranged that there would be no way for the pressurised air to access the aperture (4). An exemplary arrangement is shown on FIG. 6a, where the motor (2) has a lateral side (2a) which is flattened against the partition (5). With such an arrangement, additional air ducts (60, 61) are arranged in the partition (5) in order to bring the pressurised air to the level of the aperture (4) for providing the counter-pressure (p2) to the liquid (1). In other embodiments, the lateral side (2a) of the motor (2) is kept away from the partition (5) by appropriate distance pieces (65, 66), as illustrated on FIG. 6b. In this case, no additional air ducts are necessary: the pressurized air flows around the distance pieces (65, 66) to deliver the counter-pressure (p2) at the level of the aperture (4).

In embodiments, a gap between the rotating assembly (3) and the aperture (4) is greater than or equal to 0.01 mm and less than or equal to 5mm. Preferably said gap is greater than or equal to 0.1 mm and less than or equal to 1 mm. Such a gap offers a good compromise between the manufacturing accuracy and the power needed for generating and controlling the counter-pressure (p2). Evidently, said gap is to be understood as being the smallest distance between the aperture through which the rotating assembly extends and the rotating assembly. In case of an assembly as illustrated in FIG. 6a and 6b for example, the gap is indicated by the letter G.

The viscosimeter according to the invention may in embodiments also comprise automatic sealing means for preventing the liquid (1) from escaping through the aperture (4) following to an insufficient counter-pressure (p2), i.e. when p2 becomes smaller than p1. The counter-pressure (p2) may for example become insufficient because of a failure of the means for creating the counter-pressure, or simply because said means are voluntary deactivated for maintenance reasons.

An example of such an automatic sealing means is shown in FIG. 7. The automatic sealing means comprises a safety membrane (70) which is hermetically attached to the rotating assembly (3) and whose apparent surface overlaps the aperture (4). The safety membrane (70) is arranged in such a way that, under normal operating conditions, it is pushed away from the partition (5) by the compressed air due to the counter-pressure (p2). When the counter-pressure (p2) falls below the liquid pressure (p1) at the level of the aperture (4), the liquid (1) will automatically push the safety membrane (70) against the partition (5), thereby preventing the liquid (1) from escaping through the aperture (4). It is to be noted that since the safety membrane (70) is pushed away from the partition (5) under normal operating conditions, said membrane (70) does not generate parasitic friction forces.

In a preferred embodiment, the viscosimeter according to the invention is used for the online measurement of the viscosity of a material comprising a polymer in the course of polymerisation. The inventor has optimised the components for such an application, leading to the following characteristics:

- the motor (2) is a DC motor (2) with a nominal power of 90 W,
- the volume of air contained in the motor housing (10) is around 30 cl (centiliters),
- the counter-pressure (p2) is set at 140 kPa relative for a liquid level which is 6 m above the level of the aperture (4).

It is to be noted that other gasses than air can be used for providing the counter-pressure (p2). In case a reaction of the gas with the liquid to be tested (1) is undesirable or unacceptable, an inert gas such as nitrogen can be used.

So far, the term viscosity has been used, which is typically a property of fluids. It is to be understood that the invention also relates to apparatus for the measurement of similar properties of multi-phase materials, yet using a similar measurement principle, such as for example apparatus measuring the shear forces imparted by a slurry on a rotating part for determining the consistency of said slurry.

Evidently, the viscosimeter according to the invention may also be used in cases where the liquid level is not able to reach the level of the aperture (4), for example for measuring the viscosity of a liquid contained in a tank through an aperture (4) which is above the level which the liquid is able to reach.

In short the invention may be described as follows: Rotating type viscosimeter having a motor (2) for driving a rotating assembly (3) extending through an aperture (4) into a liquid to be tested (1) and measuring the shear forces imparted by said liquid (1) to the rotating assembly (3). In order to prevent said liquid (1) from leaking through the aperture (4) due to a liquid pressure (p1) at the level of the aperture (4), the viscosimeter comprises means for creating a counter-pressure (p2) at the level of a gap between the rotating assembly (3) and the aperture (4). Thanks to this counter-pressure (p2), no solid sealing means are required, thereby improving the durability and the robustness of the viscosimeter, as well as simplifying it by eliminating countermeasures otherwise needed for taking into account parasitic friction forces exerted on the rotating assembly (3) due to such solid sealing means.

The invention claim is:

1. Viscosimeter comprising a motor (2) for driving an assembly (3) in a rotary movement, said assembly (3) extending at least partially into a liquid to be tested (1) through an aperture (4) of a partition (5) for separating the liquid (1) from the motor (2), characterized in that the viscosimeter comprises means for creating a counter-pressure (p2) at a motor side (M) of the partition (5) for preventing the liquid (1) from escaping through the aperture (4), the level of the liquid (1) being—in operation—above the aperture (4).

2. Viscosimeter according to claim 1, further comprising means (40) for regulating the counter-pressure (p2).

3. Viscosimeter according to claim 2, characterized in that a gap between the rotating assembly (3) and the aperture (4) at the level of the aperture (4) is greater than or equal to 0.01 mm and less than or equal to 5 mm.

4. Viscosimeter according to claim 3, characterized in that the gap is greater than or equal to 0.1 mm and less than or equal to 1 mm.

5. Viscosimeter according to claim 4, further comprising automatic sealing means for preventing the liquid (1) from escaping through the aperture (4) in case the means for creating the counter-pressure (p2) at the motor side (M) of the partition (5) fail to prevent the liquid (1) from escaping through the aperture (4).

6. Viscosimeter according to claim 5, characterized in that the automatic sealing means comprise a safety membrane (70) hermetically attached to the rotating assembly (3) and in that the apparent surface of said safety membrane (70) overlaps the aperture (4).

7. Viscosimeter according to claim 6, characterized in that a medium for exerting the counter-pressure (p2) is ambient air.

8. Viscosimeter according to claim 6, characterized in that a medium for exerting the counter-pressure (p2) is an inert gas.

9. Viscosimeter according to claim 1, characterized in that a gap between the rotating assembly (3) and the aperture (4) at the level of the aperture (4) is greater than or equal to 0.01 mm and less than or equal to 5 mm.

10. Viscosimeter according to claim 9 characterized in that the gap is greater than or equal to 0.1 mm and less than or equal to 1 mm.

11. Viscosimeter according to claim 1, further comprising automatic sealing means for preventing the liquid (1) from escaping through the aperture (4) in case the means for creating the counter-pressure (p2) at the motor side (M) of the partition (5) fail to prevent the liquid (1) from escaping through the aperture (4).

12. Viscosimeter according to claim 11, characterized in that the automatic sealing means comprise a safety membrane (70) hermetically attached to the rotating assembly (3) and in that the apparent surface of said safety membrane (70) overlaps the aperture (4).

13. Viscosimeter according to claim 1, characterized in that a medium for exerting the counter-pressure (p2) is ambient air.

14. Viscosimeter according to claim 3, characterized in that a medium for exerting the counter-pressure (p2) is ambient air.

15. Viscosimeter according to claim 4, characterized in that a medium for exerting the counter-pressure (p2) is ambient air.

16. Viscosimeter according to claim 5, characterized in that a medium for exerting the counter-pressure (p2) is ambient air.

17. Viscosimeter according to claim 1, characterized in that a medium for exerting the counter-pressure (p2) is an inert gas.

18. Viscosimeter according to claim 3, characterized in that a medium for exerting the counter-pressure (p2) is an inert gas.

19. Method for measuring the viscosity of a liquid to be tested (1), comprising the steps of:
   having a motor (2) driving an assembly (3) in a rotary movement, said assembly (3) extending at least partially into the liquid to be tested (1) through an aperture (4) of a partition (5) for separating the liquid (1) from the motor (2), the level of the liquid (1) being—in operation—above the aperture (4),
   creating a counter-pressure (p2) at a motor side (M) of the partition (5) for preventing the liquid (1) from escaping through the aperture (4), and
   measuring the shear forces imparted by the liquid (1) on a part of the rotating assembly (3) in contact with the liquid (1).

20. Method for measuring the viscosity of a liquid according to claim 19, further comprising the step of regulating the counter-pressure (p2).

* * * * *

UNITED STATES PATENT AND TRADEMARK OFFICE
CERTIFICATE OF CORRECTION

PATENT NO.        : 7,073,372 B2                                Page 1 of 1
APPLICATION NO. : 10/478029
DATED             : July 11, 2006
INVENTOR(S)       : Hugues Lahaut It is certified that error appears in the above-identified patent and that said Letters Patent is hereby corrected as shown below:

The title should be -- ONLINE ROTATING VISCOSIMETER AND ASSOCIATED MEASUREMENT METHODS --

Signed and Sealed this

Twentieth Day of November, 2007

JON W. DUDAS
*Director of the United States Patent and Trademark Office*